US00PP19578P2

(12) United States Plant Patent
Delabroye

(10) Patent No.: US PP19,578 P2
(45) Date of Patent: Dec. 16, 2008

(54) ***HEUCHERA* PLANT NAMED 'ENCORE'**

(50) Latin Name: *Heuchera*
Varietal Denomination: Encore

(76) Inventor: Sandrine Delabroye, Rue Roger Salengro 40, Hantay (FR), F-59496

( * ) Notice: Subject to any disclaimer, the term of this patent is extended or adjusted under 35 U.S.C. 154(b) by 0 days.

(21) Appl. No.: 12/008,941

(22) Filed: Jan. 15, 2008

(51) Int. Cl.
*A01H 5/00* (2006.01)

(52) U.S. Cl. ..... Plt./440

(58) Field of Classification Search ..... Plt./440, Plt./263.1
See application file for complete search history.

*Primary Examiner*—Annette H Para
(74) *Attorney, Agent, or Firm*—Penny J. Aguirre

(57) ABSTRACT

A new cultivar of hybrid *Heuchera* named 'Encore', characterized by its leaves that are rose-purple in color with a silvery overlay and dark rose-purple veins with a lower leaf surface that is a vibrant red-purple in color. 'Encore' can be further characterized by its compact and mounded plant habit, its tolerance to heat and humidity and its hardiness at least in U.S.D.A Zones 4 to 9.

2 Drawing Sheets

Botanical classification: *Heuchera* hybrid.
Cultivar designation: 'Encore'.

CROSS REFERENCE TO A RELATED APPLICATION

This application is co-pending with U.S. Plant patent applications filed for sibling plants derived from the same cross in the inventor's breeding program that are entitled *Heuchera* Plant Named 'Pinot Noir' (U.S. Plant application Ser. No. 12/002,889), *Heuchera* Plant Named 'Beaujolais' (U.S. Plant patent application Ser. No. 12/008,338), *Heuchera* Plant Named 'Pinot Gris' (U.S. Plant patent application Ser. No. 12/008,928), *Heuchera* Plant Named 'Tiramisu' (U.S. Plant patent application Ser. No. 12/002,921), and *Heuchera* Plant Named 'Pistache' (U.S. Plant patent application Ser. No. 12/008,927).

BACKGROUND OF THE INVENTION

The present invention relates to a new and distinct cultivar of hybrid *Heuchera,* botanically known as a *Heuchera* of hybrid origin and is hereinafter referred to by the cultivar name 'Encore'.

The new cultivar was derived from a controlled breeding program by the inventor in Hantay, France. The inventor made a cross in summer of 2005 between *Heuchera* 'Gloire d'Orleans' (not patented, syn. *Heuchera*×*brizoides* 'Gloire d'Orleans') as the male parent and *Heuchera*×*villosa* 'Caramel' (U.S. Plant No. 16,560) as the female parent. The goal of the breeding program was to obtain unique cultivars of *Heuchera* that combined the flowering habit of 'Gloire d'Orleans' with the vigor and unique foliage coloration of *Heuchera*×*villosa.* The inventor selected 'Encore' in 2006 as a single unique plant amongst the seedlings that resulted from the above cross.

Asexual reproduction of the new cultivar was first accomplished under direction of the inventor by in vitro propagation in Rijswijk, The Netherlands in winter of 2007. Asexual reproduction of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Encore' as a new and unique cultivar of *Heuchera.*

1. 'Encore' exhibits unique foliage with leaves that emerge rose-purple in color with silver highlights and rose-purple veins, leaves are held on rose-purple petioles. The underside of the leaves are a vibrant red-purple.
2. 'Encore' exhibits medium sized, orbicular shaped leaves.
3. 'Encore' exhibits a compact, mounding plant habit.
4. 'Encore' is tolerant to high heat and humidity imparted by having *Heuchera*×*villosa* in its parentage.
5. 'Encore' is cold hardy in U.S.D.A. Zones 4 to 9.

'Encore' differs from its parent plants in that 'Caramel' is a ×*villosa* hybrid and has foliage that is yellow-orange in color and 'Gloire d'Orleans' is a ×*brizoides* hybrid with green foliage.

'Encore' can be compared to *Heuchera* 'Regina' (not patented) as the newly emerging leaves have similar coloration, however the mature leaves of 'Regina' are green in color with a silver overlay. The closest comparison plants in overall leaf shape, habit, and performance are its sibling cultivars that differ in foliage coloration; 'Pinot Noir' has dark purple-grey leaves, 'Beaujolias' has burgundy red foliage, 'Pinot Gris' has foliage that emerges orange-yellow in spring and changes to a rose color with a silvery overlay in summer, 'Tiramisu' has foliage that is yellow-green with red mottling, and 'Pistache' has yellow-green foliage.

BRIEF DESCRIPTION OF THE DRAWING

The accompanying colored photographs illustrate the overall appearance and distinct characteristics of the new *Heuchera.* The photographs were taken in mid summer of plants six months in age as grown outdoors in a 3-liter container in The Netherlands.

The photograph on the first sheet provides a view of the plant habit and typical mid summer coloration of the new and mature foliage of 'Encore'.

The photograph on the second sheet provides a close-up view of a young leaf of 'Encore'.

The colors in the photographs are as close as possible with the photographic and printing technology utilized. The color values cited in the detailed botanical description accurately describe the colors of the new *Heuchera*.

DETAILED BOTANICAL DESCRIPTION OF THE PLANT

The following is a detailed description of six month-old plants of the new cultivar grown two in a 3-liter container outdoors in The Netherlands. Plants were grown under average day temperatures of 12° to 28° C. and average night temperatures of 5 to 14° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Plant habit.*—Compact, clump-forming, mounded, herbaceous perennial.

*Height and spread.*—Reaches a height of about 16.4 cm in height and about 36.7 cm in width.

*Hardiness.*—At least U.S.D.A. Zone 4 to 9.

*Culture.*—Full sun to medium shade in moist, well-drained, fertile soils, tolerant to high heat and humidity.

*Diseases and pests.*—Disease free in the conditions tested, no susceptibility or resistance to pests has been observed.

*Root description.*—Fibrous roots on woody rootstalks.

*Branching habit.*—Basal rosettes of leaves on petioles.

*Propagation.*—In vitro propagation is the preferred method, division are also possible.

*Root initiation.*—Roots appear in rooting media in 10 day at 20° C. in the laboratory without supplemental lighting.

*Root development.*—Rooted transplants from tissue culture fully develop in a 2.5 inch container in about 20 days in a greenhouse with average temperatures of about 20° C. without supplemental lighting in The Netherlands.

*Growth rate.*—Moderate, grows about 5 cm per month in spring, with an average crop time of 20 weeks to develop in a 9 cm container.

Foliage description:

*Leaf shape.*—Orbicular in overall shape.

*Leaf division.*—Simple.

*Leaf base.*—Hastate, moderately overlapping.

*Leaf apex.*—Rounded with abruptly acute tip about 0.5 mm in length.

*Leaf venation.*—Primary palmate, secondary net-veined, conspicuous on upper surface, vein color on upper surface 176A to 178A and 146B when mature, vein color on lower surface 187D.

*Leaf margins.*—Lobed with an average of 5 lobes per leaf, lobe margin crenate.

*Leaf attachment.*—Petiolate.

*Leaf arrangement.*—Basal rosettes.

*Leaf orientation.*—Held nearly horizontal to petiole and slightly curled downward with maturity.

*Leaf surface.*—Upper and lower sides and margin sparsely covered with short hairs, average of 0.5 mm in length and 155C in color, slightly rough to touch.

*Leaf color.*—Young upper and lower surface; 187B to 187C with overlay between veins of 190D, maturing upper surface: 177D with conspicuous veins and overlay of between veins of 190D; mature lower surface; 187D.

*Leaf size.*—Average of 8.9 cm in length and 8.5 in width.

*Leaf quantity.*—Average of 31 leaves as grown in a 3-liter container.

*Petioles.*—Round in shape, average of 14.2 cm in length and 2 mm in width, 185C in color, surface is moderately covered with short hairs; average of 1.5 mm in length and 155C in color.

*Stipules.*—None.

Flower and seed description: Flowering plants were not available for data collection, racemes of white to pink bell-shaped flowers typical of *Heuchera* should be expected under the right conditions for flowering as they were reported to be observed on the original plant.

It is claimed:

1. A new and distinct cultivar of *Heuchera* plant named 'Encore' as herein illustrated and described.

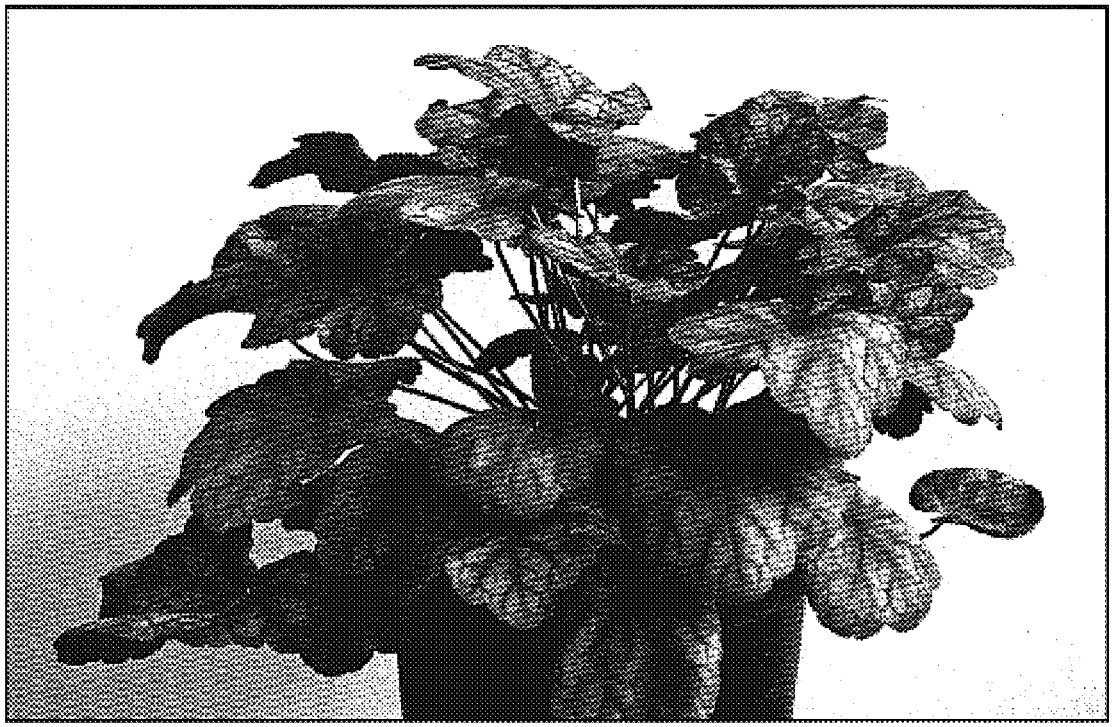

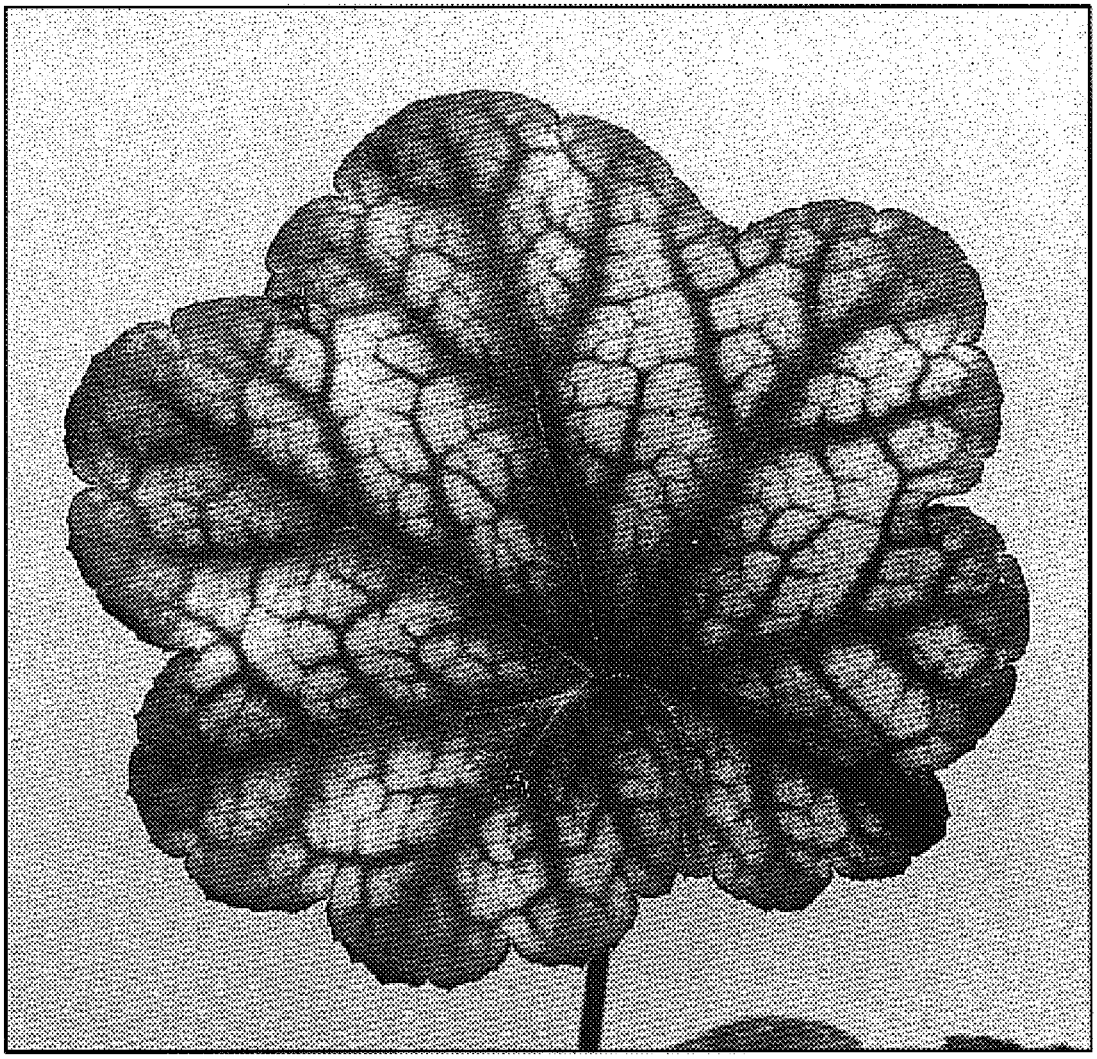

* * * * *